US00PP33585P2

(12) United States Plant Patent
de Groot

(10) Patent No.: US PP33,585 P2
(45) Date of Patent: Nov. 2, 2021

(54) ***ROSA* PLANT NAMED 'RUIRI0023A'**

(50) Latin Name: *Rosa hybrida*
Varietal Denomination: RUIRI0023A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 17/172,815

(22) Filed: Feb. 10, 2021

(51) Int. Cl.
*A01H 5/02* (2018.01)
*A01H 6/74* (2018.01)

(52) U.S. Cl.
USPC ..... Plt./108

(58) Field of Classification Search
USPC ..... Plt./101, 102, 108
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct groundcover *Rosa* plant named 'RUIRI0023A' is disclosed, characterized by abundant double red flowers with yellow stamens. Plants are compact and low growing, suitable for groundcover use. The new variety is a *Rosa*, normally produced as an outdoor garden or container plant.

2 Drawing Sheets

Figure 1:
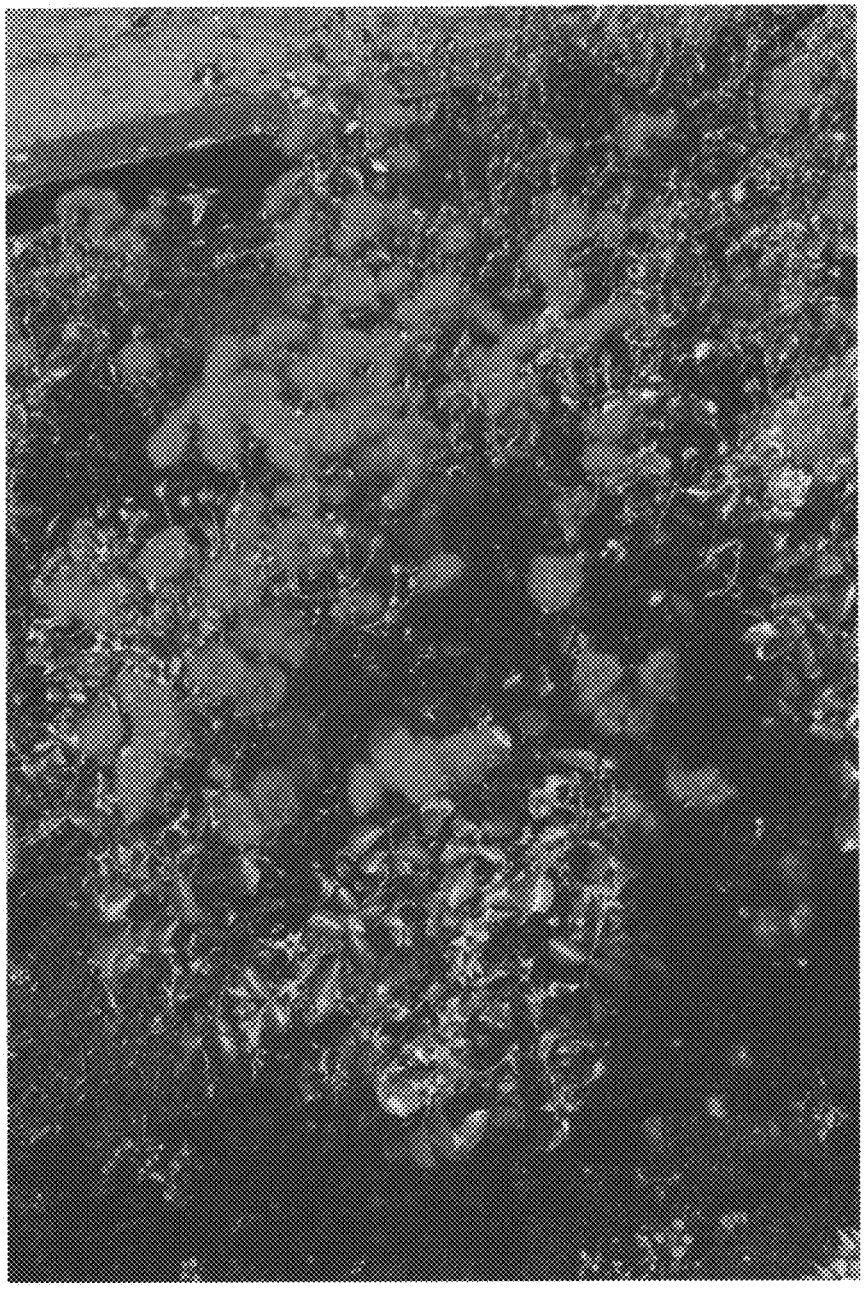

Latin name of the genus and species: *Rosa hybrida.*
Variety denomination: 'RUIRI0023A'.

BACKGROUND OF THE INVENTION

The new *Rosa* cultivar is a product of a planned breeding program conducted by the inventor. The cross resulting in this new variety was made in Spring of 2008 at a nursery in Boskoop, The Netherlands.

The seed parent is the unpatented variety *Rosa* 'NOA84497D'. The pollen parent is the unpatented variety *Rosa* 'NOACAS x TANANASTRUA'. The new variety was selected in May 2011 by the inventor at the same nursery in Boskoop, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Amstelveen, The Netherlands, in May 2011, and has shown that the unique features of this cultivar are stable and reproduced true to type in successive generations.

SUMMARY OF THE INVENTION

The cultivar 'RUIRI0023A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRI0023A' These characteristics in combination distinguish 'RUIRI0023A' as a new and distinct *Rosa* cultivar:

1. Compact, groundcover shrub rose.
2. Abundant double red flowers.
3. Yellow filament color.
4. Green receptacle color.

PARENTAL COMPARISON

Plants of the new cultivar 'RUIRI0023A' are similar to plants of the seed parent, in most horticultural characteristics, however, plants of the new cultivar 'RUIRI0023A' differ in the following:

1. Flowers of the new variety are red, while flowers of the seed parent are red-orange.

Plants of the new cultivar 'RUIRI0023A' are similar to plants of the pollen parent in most horticultural characteristics, however, plants of the new cultivar 'RUIRI0023A' differs in the following;

1. Filament color of the new variety is yellow, while the filament color of the pollen parent is red.
2. The receptacle color of the new variety is green, while the receptacle color of the pollen parent is purple.

COMMERCIAL COMPARISON

Plants of the new cultivar 'RUIRI0023A' can be compared to the commercial variety *Rosa* 'Wekcisbako', U.S. Plant Pat. No. 18,552. These varieties are similar in most horticultural characteristics, however 'RUIRI0023A' differs in the following:

1. This new cultivar has smaller flowers than this comparator.
2. This new cultivar typically produces 25 petals per flower; this comparator produces 5 petals per flower.
3. The new variety has a slower flowering cycle than this comparator.

Plants of the new cultivar 'RUIRI0023A' can be compared to the commercial variety *Rosa* 'NOA83100', U.S. Plant Pat. No. 17,373. These varieties are similar in most horticultural characteristics, however 'RUIRI0023A' differs in the following:

1. This new cultivar produces more flowers per plant than this comparator.
2. This new cultivar has a more compact, dense habit than this comparator.

BRIEF DESCRIPTION OF THE PHOTOGRAPHS

The accompanying photograph in FIG. 1 illustrates in full color typical plants of 'RUIRI0023A' in the ground, outdoors in a test field in De Kwakel, the Netherlands. Plants in FIG. 1 are approximately 2 years old.

Figure 2:
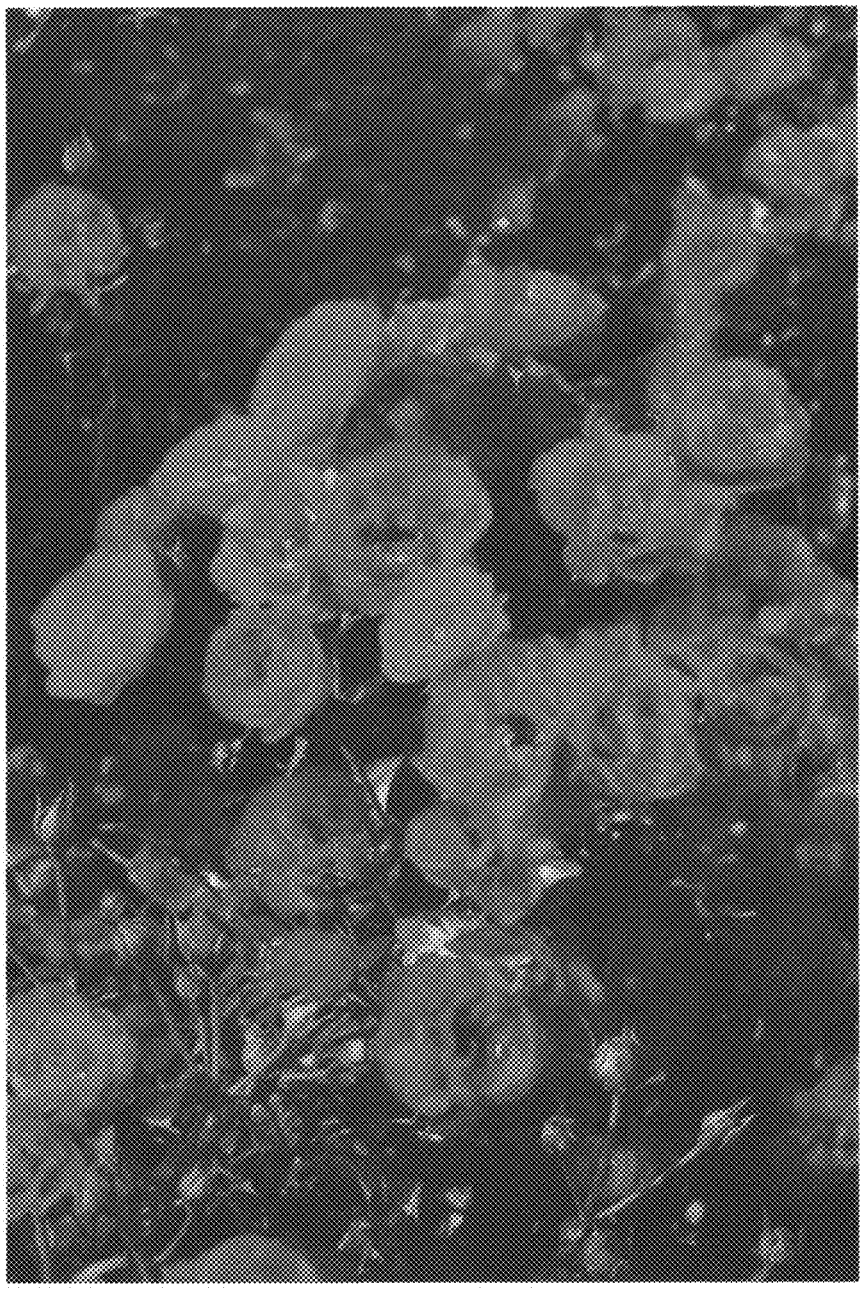

FIG. 2 illustrates a close up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRI0023A' plants grown outdoors, in De Kwakel, The Netherlands. The growing temperature ranged from approximately 20° C. to 26° C. during the day and from approximately 16° C. to 18° C. during the night. Measurements were taken in August. General light conditions were very bright, normal sunlight. Measurements and numerical values represent averages of typical plant types.

Botanical classification: *Rosa* 'RUIRI0023A'.

*Market classification*.—Bed.

PROPAGATION

Time to initiate roots: 10 days at approximately 25° C.

Time to produce a rooted cutting: 21 days at approximately 25° C.

PLANT

Growth habit: Dense, low growing, groundcover type.

Age of plant described: 1 year.

In a container or in the ground: Ground.

Height: 40 cm.

Plant spread: 30 cm.

Branching characteristics:

Length of primary lateral branches: Approximately 15 cm.

Diameter of lateral branches: Approximately 4 cm.

Quantity of lateral branches: Numerous.

Branching arrangement: Compound.

Branches-young wood:

*Diameter*.—Approximately 0.2 cm.

*Texture*.—Smooth.

*Approximately density/quantity of thorns*.—Normal.

*Color*.—Near RHS Red-Orange 174D.

Branches-old wood:

*Diameter*.—Approximately 0.5 cm, after 0.5 years.

*Color*.—Near RHS Yellow-Green 146B.

*Texture*.—Smooth.

*Density*.—Dense.

*Thorns*.—Color: Near RHS Greyed-Purple 183C. Height: 0.6 cm. Diameter: 0.5 cm.

FOLIAGE

Leaf:

*Arrangement*.—Imparipinnate.

*Quantity*.—Approximately 5 per main branch.

*Average length*.—Approximately 8 cm.

*Average width*.—Approximately 5 cm.

Leaflet:

*Quantity*.—3, 5, or 7 per leaf.

*Average length*.—Approximately 3 cm.

*Average width*.—Approximately 2.5 cm.

*Shape of blade*.—Elliptic.

*Apex*.—Acute.

*Base*.—Obtuse.

*Margin*.—Serrate.

*Texture of top surface*.—Smooth.

*Texture of bottom surface*.—Smooth.

*Pubescence*.—Puberulous.

*Leaf internode length*.—1.5-2 cm.

*Color*.—Young foliage upper side: Near RHS Green N137A. Young foliage under side: Near RHS Yellow-Green 147B. Mature foliage upper side: Near RHS Green NN137A. Mature foliage under side: Near RHS Green 147B.

*Venation*.—Type: Pinnate. Venation color upper side: Near Green 143C. Venation color under side: Near Green 138B.

Stipule:

*Length*.—1 cm.

*Width*.—0.4 cm.

*Color*.—Near RHS Green N137A.

*Texture*.—Smooth.

Petiole:

*Length*.—0.8 cm.

*Width*.—0.18 cm.

*Color*.—Near RHS Green 137B.

*Texture*.—Hairy.

Rachis:

*Length*.—1 cm.

*Width*.—0.2 cm.

*Color*.—Near RHS Yellow-Green 144C.

*Texture*.—Pubescent.

FLOWER

Natural flowering season: June-October in Europe.

Begins flowering after how many years/months: 2 months.

Inflorescence type: Multiflora.

Rate of flower opening: Approximately 3 days from bud to fully opened flower.

Flower longevity on plant: 7 days, after fully opened.

Quantity of flowers: 6 flowers per multiflora.

Inflorescence size:

*Diameter*.—Approximately 10 cm.

*Length*.—Approximately 10 cm.

Flower size:

*Diameter*.—Approximately 4.0 to 4.8 cm.

*Length*.—Approximately 3.0 cm.

Peduncle:

*Length*.—4.3 cm.

*Diameter*.—0.2 cm.

Petals:
*Petal arrangement*.—Loose.
*Length*.—1.5 cm.
*Width*.—1.5 cm.
*Shape*.—Obcordate.
*Margin*.—Undulate.
*Apex*.—Retuse.
*Base*.—Cuneate.
*Petal quantity*.—25.
*Texture*.—Velvet.
*Color*.—When opening: Upper surface: Near RHS Red 45B. Lower surface: Near RHS Red 45D. Fully opened: Upper surface: Near RHS Red 45B. Lower surface: Near RHS Red 45D. Color Changes when aging: No.

Bud:
*Shape*.—Round.
*Length*.—Approximately 1.5 cm.
*Diameter*.—Approximately 1.5 cm.
*Color*.—Near RHS Red 45D.

Sepals:
*Length*.—1.8 cm.
*Width*.—0.7 cm.
*Shape*.—Lorate.
*Color*.—Interior Surface: Near Green 138B. Exterior Surface: Near Green 138C.
*Texture*.—Smooth.

Receptacle:
*Length*.—0.5 cm.
*Width*.—0.5 cm.
*Shape*.—Round.
*Color*.—Near Yellow-Green 144D.

Fragrance: None.

REPRODUCTIVE ORGANS

Stamens:
*Quantity*.—Average 50.
*Filament length*.—Average 0.5 cm.
*Filament color*.—Yellow 9B.

Anthers:
*Length*.—2 mm.
*Shape*.—Oblong.
*Color*.—RHS Yellow-Orange 22A.

Pistil:
*Number*.—Approximately 20.
*Length*.—6 mm.
*Style*.—Length: Approximately 0.5 cm. Color: Near RHS Yellow-Green 149D.

Stigma:
*Shape*.—Orbicular.
*Color*.—RHS Greyed-Yellow 160D.

OTHER CHARACTERISTICS

Seeds and fruits: Not observed.

What is claimed is:

1. A new and distinct hybrid cultivar of *Rosa* plant named 'RUIRI0023A' as herein illustrated and described.

* * * * *